United States Patent
Brainard, II (10) Patent No.: US 7,547,284 B2
(45) Date of Patent: Jun. 16, 2009

(54) BILATERAL DIFFERENTIAL PULSE METHOD FOR MEASURING BRAIN ACTIVITY

(75) Inventor: Edward C Brainard, II, Marion, MA (US)

(73) Assignee: Atlantis Limited Partnership, Marion, MA (US)

( * ) Notice: Subject to any disclaimer, the term of this patent is extended or adjusted under 35 U.S.C. 154(b) by 119 days.

(21) Appl. No.: 11/664,688

(22) PCT Filed: Jan. 12, 2006

(86) PCT No.: PCT/US2006/000817

§ 371 (c)(1),
(2), (4) Date: Apr. 5, 2007

(87) PCT Pub. No.: WO2006/076361

PCT Pub. Date: Jul. 20, 2006

(65) Prior Publication Data

US 2008/0021332 A1        Jan. 24, 2008

Related U.S. Application Data

(60) Provisional application No. 60/643,627, filed on Jan. 14, 2005.

(51) Int. Cl.
*A61B 5/02* (2006.01)
*A61B 8/00* (2006.01)

(52) U.S. Cl. .................. 600/500; 600/483; 600/481; 600/454; 600/479; 600/437

(58) Field of Classification Search .............. 600/544, 600/545, 500–504, 481, 483, 323, 324
See application file for complete search history.

(56) References Cited

U.S. PATENT DOCUMENTS

| | | | |
|---|---|---|---|
| 5,119,815 A * | 6/1992 | Chance | 600/433 |
| 5,779,631 A * | 7/1998 | Chance | 600/328 |
| 5,792,051 A | 8/1998 | Chance | |
| 5,873,821 A * | 2/1999 | Chance et al. | 600/310 |
| 5,954,053 A * | 9/1999 | Chance et al. | 600/310 |
| 6,192,260 B1 * | 2/2001 | Chance | 600/310 |
| 6,334,065 B1 * | 12/2001 | Al-Ali et al. | 600/323 |
| 6,526,297 B1 | 2/2003 | Merilainen | |
| 6,549,795 B1 * | 4/2003 | Chance | 600/340 |
| 6,564,076 B1 * | 5/2003 | Chance | 600/310 |
| 6,615,065 B1 * | 9/2003 | Barrett et al. | 600/340 |
| 6,714,804 B2 * | 3/2004 | Al-Ali et al. | 600/323 |
| 6,785,568 B2 * | 8/2004 | Chance | 600/340 |
| 6,836,680 B2 * | 12/2004 | Kuo | 600/513 |
| 6,898,452 B2 * | 5/2005 | Al-Ali et al. | 600/323 |

* cited by examiner

*Primary Examiner*—Charles A Marmor, II
*Assistant Examiner*—Navin Natnithithadha
(74) *Attorney, Agent, or Firm*—Young & Thompson (57) ABSTRACT

A method of measuring human brain activity includes the steps of simultaneously measuring pulses at two locations on a human subject that each receives blood from a different carotid artery that feeds a respective one of left and right hemispheres of the brain of the human subject, determining pulse characteristics from the measured pulses, and evaluating relative left and right hemisphere activity of the brain of the human subject based on the determined pulse characteristics. The method may use dual photoplethysmograhic blood pulse sensors that measure left and right hemisphere activity by determining pulse amplitude difference and time or phase differences between the earlobes while the subject carries out various mental functions. The data from the sensors are processed to provide a measure of brain function and the mental activity of the subject.

20 Claims, 7 Drawing Sheets

BILATERAL DIFFERENTIAL PULSE METHOD FOR MEASURING BRAIN ACTIVITY

BACKGROUND OF THE INVENTION

The present invention relates to a method of measuring brain activity using blood pulse sensors.

The method of the present invention is based on the principle that the flow of blood through the tissues of the body varies with the level of metabolism and functional activity in these tissues. The increased functional level in a tissue can only be sustained by increasing the rate at which oxygen is consumed. The oxygen is delivered by blood flow. Most of the usable energy in the body comes from splitting the energy-rich molecule adenosine triphosphate (ATP) into adenosine diphosphate (ADP) and inorganic phosphate ($P_I$). ATP is then reconstituted from its split products in a reaction requiring oxygen and glucose (Oxidative Phosphorylation).

Because there is a constant ratio between the number of ATP molecules regenerated and the number of oxygen molecules taken up in the process, the functional level of a tissue is tightly coupled to its oxygen uptake. Oxygen is supplied to the tissues by the bloodstream. A rise in oxygen demand is met by an increased flow of oxygenated blood. For example, increased mental activity in the brain can double the flow of blood to the brain. The major supply of blood to the brain is through the left and right carotid arteries, while lesser amounts of blood are delivered to the rear of the brain through the vertebral arteries.

The desire to understand the activity and function of the brain has consumed the mind of man since the beginning of recorded history. With the advent of the electronic amplifier, attempts have been made and steadily improved in technique to measure brain waves. Electroencephalogram, EEG, recordings were first made in the 1930s. The measurements involved placing electrodes on the scalp and recording weak electrical signals due to the firing of neurons within the brain. Most recently, a soft helmet containing a multitude of electrodes has been employed. The electrode outputs are digitally processed to give an automatic analysis of brain function. A major problem with EEG techniques is that the electrodes must make good and continuous contact with the scalp, and the electrical signals are very weak, i.e. 1 microvolt. Hair can cause considerable electrical contact problems. A gel must be used to improve the electrical contact. The electrodes must not move during the measurement period or else the reliability of the analysis will be jeopardized.

The use of radioactive tracers to investigate internal brain function was first introduced in the 1960s. It has since been highly developed and has become a general radiological tool in medicine. The technique is called Positron Emission Tomography, PET. PET is a technique for measuring blood flow and metabolism of internal body tissue including the heart and brain. The technique traces emission from an injected radioactive substance to generate images of activity at specific brain receptors. A very small amount of a glucose radio labeled compound is injected into the patient. The injected compound accumulates in the tissue to be studied, especially where there is high metabolic activity. As the radioactive atoms in the compound decay, they release smaller particles called positrons, which are positively charged. When a positron collides with an electron (negatively charged), they are both annihilated, and two photons (light particles) are emitted. The photons move in opposite directions and are picked up by the detector ring of the PET scanner. A computer uses this information to generate three-dimensional, cross-sectional images that represent the biological activity where the radio labeled compound has been accumulated. Using PET, brain areas can be located where specific brain functions occur.

PET provides a significant amount of information on brain function, but the equipment is large, complex and the technique uses radioactive isotopes, which carry a certain amount of risk for the subject.

Functional Magnetic Resonance Imagine, fMRI, uses nuclear magnetic resonance of protons to produce proton density maps of the brain. It is a non-invasive procedure that produces a 3-D view of the brain. The technique does not involve X-radiation or the use of radioisotopes. It produces better imaging of soft tissue than X-radiation, and has no reported danger for the subject. However, the method involves the use of a large and cumbersome apparatus, which is very expensive.

The above methods all produce internal imaging of the brain and have formed a valuable tool for brain function study, such as for left and right hemisphere usage, information for educational instruction, employee evaluation, lie detection, work load, and sleep detection.

The medical literature abounds with articles describing cardiovascular instrumentation for evaluation of blood flow in the human body. A variety of sensors have been used including EKG electrode sensors, acoustic stethoscopes, acoustic Doppler flow sensors, pressure sensors, accelerometers, and photoplethysomographic infrared pulse sensors called Pleths. These sensors have been used to monitor blood flow between the heart, toes, fingers, earlobes, and other sites. Detailed analysis has been performed in the time domain to determine pulse magnitude comparisons, and time delays.

Allen and Murray (Allen, J. and Murray, A., "Variability of photoplethysmography peripheral pulse measurements: thumbs and toes", IEE Pro. Sci. Meas. Technol./Vol. 147. No. 6 November 2000) provide a detailed account of delay times between ears, thumbs, and toes. The same authors provide age-related changes in the characteristics of the photoplethysmographic pulse shape at similar body locations. All these measurements involve measurements at the heart and at the external body sites.

Allen and Murray further explored this area (Allen, J. and Murray, A., "Similarity in bilateral photophlethysmorgraphic peripheral pulse wave characteristics at the ears, thumbs and toes," Physiol. Meas. 21, 369-377, 2000) and describe placing Pleth sensors at pairs of peripheral body sites, including ears, thumbs and big toes. The measurements are used to detect vascular abnormalities.

Swift and Perlman (Swift A. B. and Perlman M. B., "A Noninvasive Index of Hemispheric Activity" Perceptual and Motor Skills, 1985, 60, 515-524), following a suggestion by the present inventor who also supplied the tympanic temperature instrumentation for the experiment, have published a paper entitled "A Noninvasive Index of Hemispheric Activity." Two tympanic temperature sensors were inserted into a subject's ear canals where they rested near or against the tympanic membrane. The sensors thus gave an estimate of the brain core temperature, which increased with mental activity. The subject was then run through a series of tests, which stimulated cortical activity in the left and right hemispheres. This work showed some interesting results but was not definitive since the tympanic temperature sensors had a slow response, and body motion, such as a cough, could give significant errors.

U.S. patents that discuss this subject include U.S. Pat. No. 3,734,086 of May 22, 1973; U.S. Pat. No. 3,908,640 of Sep. 30, 1975; U.S. Pat. No. 4,425,922 Jan. 17, 1984; U.S. Pat. No.

4,807,638 of Feb. 28, 1989; U.S. Pat. No. 5,293,874 of Mar. 15, 1994; U.S. Pat. No. 5,365,930 of Nov. 22, 1994; U.S. Pat. No. 6,331,159 of Dec. 18, 2001; and U.S. Pat. No. 6,537,226 of Mar. 25, 2003.

SUMMARY OF THE INVENTION

An object of the present invention is to provide a novel method of measuring brain activity of a human subject that is noninvasive and avoids the above-noted problems of the prior art.

A further object of the present invention is to provide a novel method of measuring human brain activity that simultaneously measures pulses at two locations on a human subject that each receives blood from a different carotid artery or branch thereof that feeds a respective one of left and right hemispheres of the brain of the human subject, determines pulse characteristics from the measured pulses, and evaluates relative left and right hemisphere activity of the brain of the human subject based on the determined pulse characteristics.

A yet further object of the present invention is to provide a method of measuring human brain activity in which the pulse of the human subject is simultaneously measured at three locations, the first and second locations each receiving blood from a different carotid artery or branch thereof that feeds a respective one of left and right hemispheres of the brain of the human subject and the third location being adjacent to the heart of the human subject, and in which the relative and absolute left and right hemisphere activity of the brain of the human subject is evaluated based on characteristics of the pulses.

In a preferred embodiment, the method is a technique for monitoring left and right brain activity using two photoplethysomographic infrared pulse (Pleth) sensors on the left and right earlobes of a human subject. The measurements are made simultaneously to provide a differential measurement of the pulse amplitude at each earlobe. The earlobe is fed blood from a branch artery of the carotid artery, the external carotid artery. The carotid arteries form a major blood supply system for nourishing the left and right brain hemispheres. The pulse measurements are an approximation of hemispheric brain activity. The signals from the Pleth sensors are either processed using analog techniques in the time domain to analyze pulse amplitude and time difference between the left and right earlobes, or digitized and further processed. The digital processing can be in the time domain to give amplitude and time delay values, or autocorrelation techniques can be used to provide a frequency spectrum with pulse time delay information. The digital signal can be processed with the Fast Fourier Transform, FFT, or other deconvolution software. The computed real and imaginary components are processed to give such key values as the amplitude at the peak pulse frequency, ratio of the amplitudes between the left and right ears, and the phase angles and time difference between Pleth sensors.

These and other objects and advantages of the invention will be apparent to those of skill in the art of the present invention after consideration of the following drawings and description of preferred embodiments.

DESCRIPTION OF PREFERRED EMBODIMENTS

The present invention is based on the fact that measurement of blood flow on the earlobes, neck and forehead directly reflects the blood flow to the brain through the carotid arteries. The carotid arteries and branches thereof feed blood to the face and scalp, including the ears, forehead and jaw. Blood flow to these areas is not constricted differently than to the carotid arteries, and thus a measurement of blood flow at these areas is a measurement of a relative flow of blood to the brain. The simultaneous measurement at two sides of the head gives a measurement of differential functioning of the left and right hemispheres of the brain.

One embodiment of the method of measuring human brain activity according to the present invention includes the steps of simultaneously measuring pulses at two locations on a human subject that each receives blood from a different carotid artery or branch thereof that feeds a respective one of left and right hemispheres of the brain of the human subject, determining pulse characteristics from the measured pulses, the pulse characteristics including (1) amplitudes of the measured pulses, (2) differences between the amplitudes of the measured pulses, and (3) time differences between the measured pulses, and evaluating relative left and right hemisphere activity of the brain of the human subject based on the determined pulse characteristics.

A further embodiment of the method includes pulse measurements at three locations, the third location being adjacent to the heart of the human subject, to provide yet greater accuracy. The further embodiment includes the steps of simultaneously measuring pulses at three locations on a human subject, the first and second locations each receiving blood from a different carotid artery or branch thereof that feeds a respective one of left and right hemispheres of the brain of the human subject, and the third location being adjacent to the heart of the human subject, determining pulse characteristics from the measured pulses, and evaluating relative and absolute left and right hemisphere activity of the brain of the human subject based on the determined pulse characteristics.

Each of these embodiments may be further defined wherein the step of measuring pulses includes placing pulse sensors on left and right earlobes of the human subject. The pulse sensors may be of the type that transmits infrared energy through the respective earlobe. Alternatively, the pulse sensors may be placed on left and right sides of a forehead of the human subject or on left and right sides of a neck of the human subject adjacent to the respective carotid artery or branch thereof.

The method may further include disproportionately stimulating brain activity in the left and right hemispheres of the brain of the human subject during the step of measuring pulses. The human subject may be in motion or prone, standing or sitting during the evaluation.

The measured pulses may be wirelessly transmitted to a receiver remote from the human subject during the step of measuring pulses, and the steps of determining and evaluating brain activity may be carried out with a processor attached to the receiver.

The method may be enhanced by the further step of setting results of measurements at the two locations equal to each other during a period of mental relaxation of the human subject before the step of measuring pulses.

Figure 1:
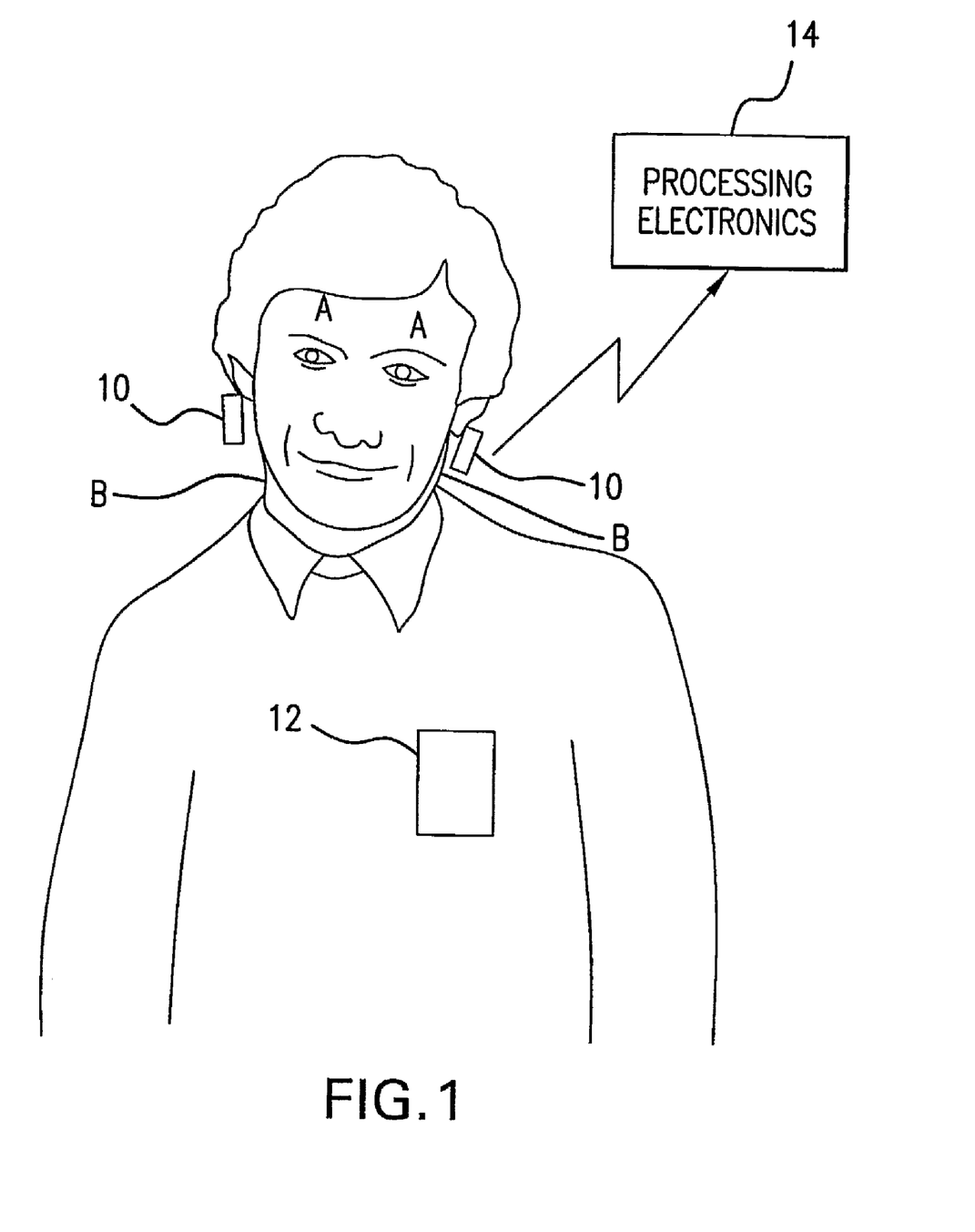
FIG. 1 is a pictorial representation depicting placement of the pulse sensors on a human subject in embodiments of the present invention.

FIG. 1 shows the installation of sensors on a human subject. Two sensors 10 may be placed on the left and right earlobes. In alternative embodiments, the sensors 10 may be placed on the forehead (indicated at locations A) or on the neck adjacent to the respective carotid artery or branch thereof (indicated at locations B). In the further embodiment, an additional sensor 12 is placed on the chest over the heart. The sensors communicate their readings to processing electronics 14, which may be digital or analog. The communication may be wired or wireless. The sensors 10 may be Pleth sensors or other suitable optical sensors, RF displacement sensors, capacitance displacement sensors, pressure sensors, acoustic distance sensors, acoustic Doppler flow sensors, and optical displacement sensors.

In the embodiments of the present invention, the signals from the sensors are either processed using analog techniques in the time domain to analyze pulse amplitude and time difference between the left and right earlobes, or digitized and further processed. The digital processing can be in the time domain to give amplitude and time delay values, or autocorrelation techniques can be used to provide a frequency spectrum with pulse time delay information. The digital signal can be processed with the Fast Fourier Transform, FFT, or other deconvolution software. The computed real and imaginary components are processed to give such key values as the amplitude at the peak pulse frequency, ratio of the amplitudes between the left and right ears, and the phase angles and time difference. The use of the FFT is the preferred method due to simplicity, versatility, and reduction of noise by using the energy at the fundamental frequency of the heart pulse. A DC bias outside a 0.75-2.0 Hz operating band may be removed during the processing in order to reject low frequency noise that may be caused by motion or physiological changes of the subject.

Figure 2:
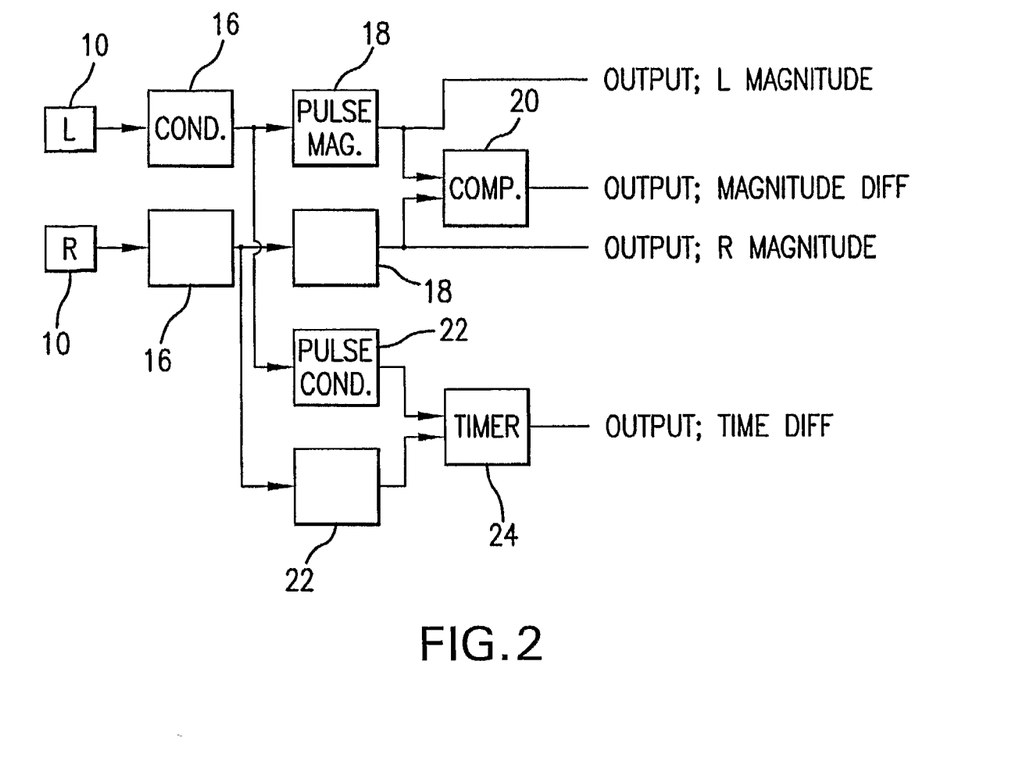
FIG. 2 is a block diagram of an analog signal processing flow for a two sensor embodiment of the present invention.

FIG. 2 is a block diagram of the analog processing electronics for the two-sensor embodiment. The left sensor 10 feeds an analog conditioning circuit 16 which provides suitable power for the sensor, signal conditioning amplifier, and high and low pass filters to eliminate noise in a typical test area. The subsequent pulse magnitude detection circuit 18 measures the pulse magnitude, and feeds it to a pulse comparator circuit 20. Similarly, the right sensor 10 feeds its output to pulse comparator circuit 20. The output of pulse comparator circuit 20 includes magnitudes of the pulses measured by the sensors 10 and the difference between these pulse magnitudes. The output may be recorded on a suitable device such as an analog meter, digital meter or strip chart recorder. In addition, the pulse outputs from the analog circuitry 16 are conditioned in waveform by pulse conditioners 22 and fed to a timer 24. The output of timer 24 is the time difference between the arrival times of the pulses at the sensors 10.

Figure 3:
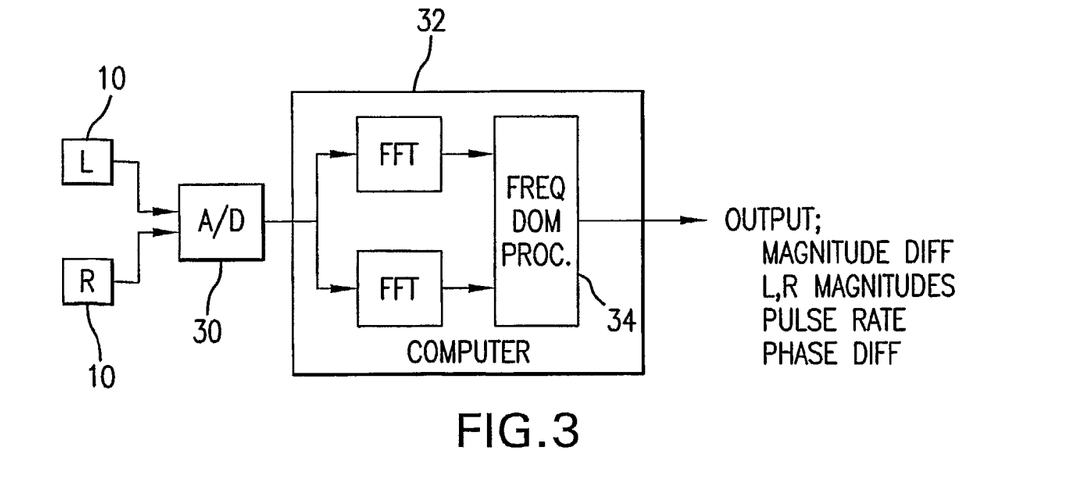
FIG. 3 is a block diagram of a digital signal processing flow for a two sensor embodiment of the present invention.

With reference to FIG. 3, the pulse signals from sensors 10 can also be processed using digital techniques. A/D converter 30 digitizes the pulse outputs and feeds the resulting signal to a computer 32, which may be any suitable processor, such as a PC or laptop computer. The computer 32 conditions the digitized pulse outputs with a Hanning filter. Then the time series is processed using a Fast Fourier Transform (FFT) algorithm and the processed data are passed to processor 34. The frequency domain data series are then processed by frequency domain software in processor 34 to provide outputs that include pulse magnitude difference, left sensor magnitude, right sensor magnitude, pulse rate, and phase difference. The phase difference can be converted to time delay by relating it to the pulse frequency using simple mathematical calculations.

Figure 4A:
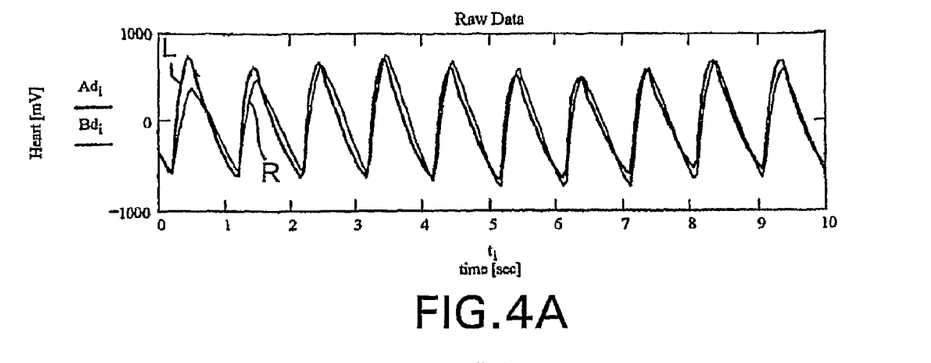
FIGS. 4A-D are graphs showing outputs from the time and frequency domain processing of the pulse outputs for the two sensor embodiment in a baseline condition when a subject is at rest (FIGS. 4A-B) and in a stimulated condition when solving a math problem (FIGS. 4C-D).
Figure 4B:
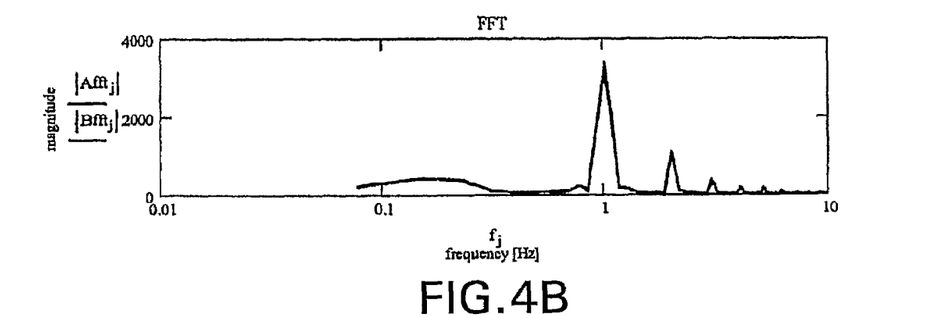
Figure 4C:
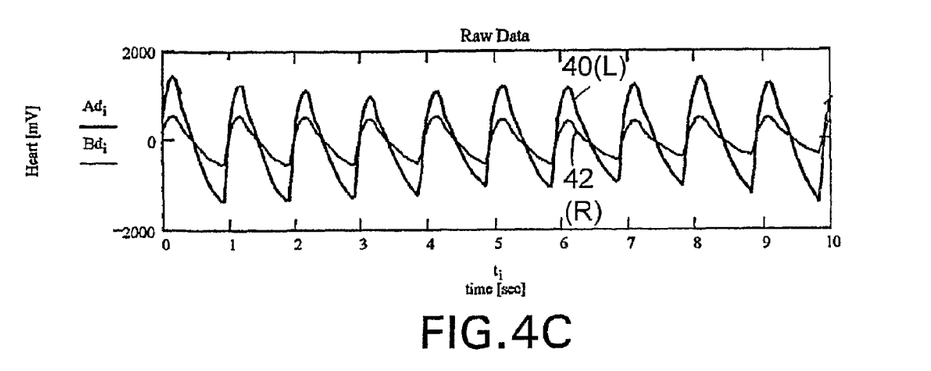
Figure 4D:
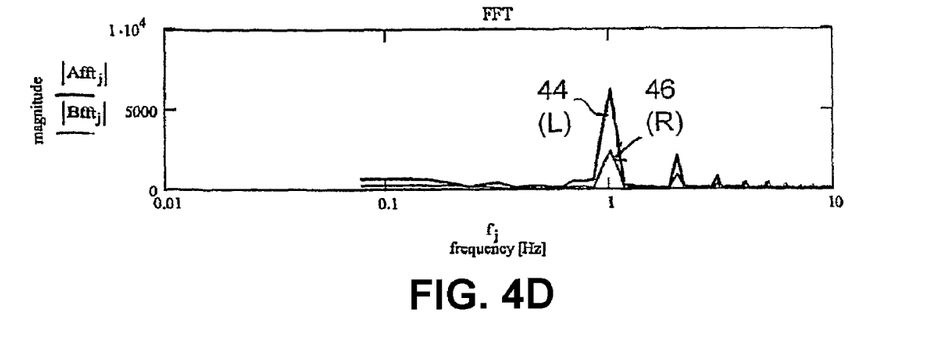

FIGS. 4A-D are graphs showing outputs from the time and frequency domain processing of the pulse outputs for the two sensor embodiment in a baseline condition when the subject is at rest (FIGS. 4A-B) and in a stimulated condition when the subject is solving a math problem (FIGS. 4C-D). FIG. 4A shows the output of the two sensors as a time series graph over 10 seconds. FIG. 4B shows the magnitude of pulses that have been processed using the FFT. The frequency scale is from 0.01 to 10 Hz. Since these measurements were made with the subject at rest while supine, they are approximately the same magnitude. In FIG. 4B, the magnitude is read at the peak at approximately 1 Hz. The smaller higher frequency peaks are harmonic resonances in the arterial system including the heart. FIG. 4C shows a time series 40 for the left sensor and a time series 42 for the right sensor when the subject was taking a math test (sequentially subtracting 9 from 200 and from the resultant remainder). FIG. 4D shows the frequency domain representation of the data during the math test for the left sensor 44 and the right sensor 46.

Figure 5:
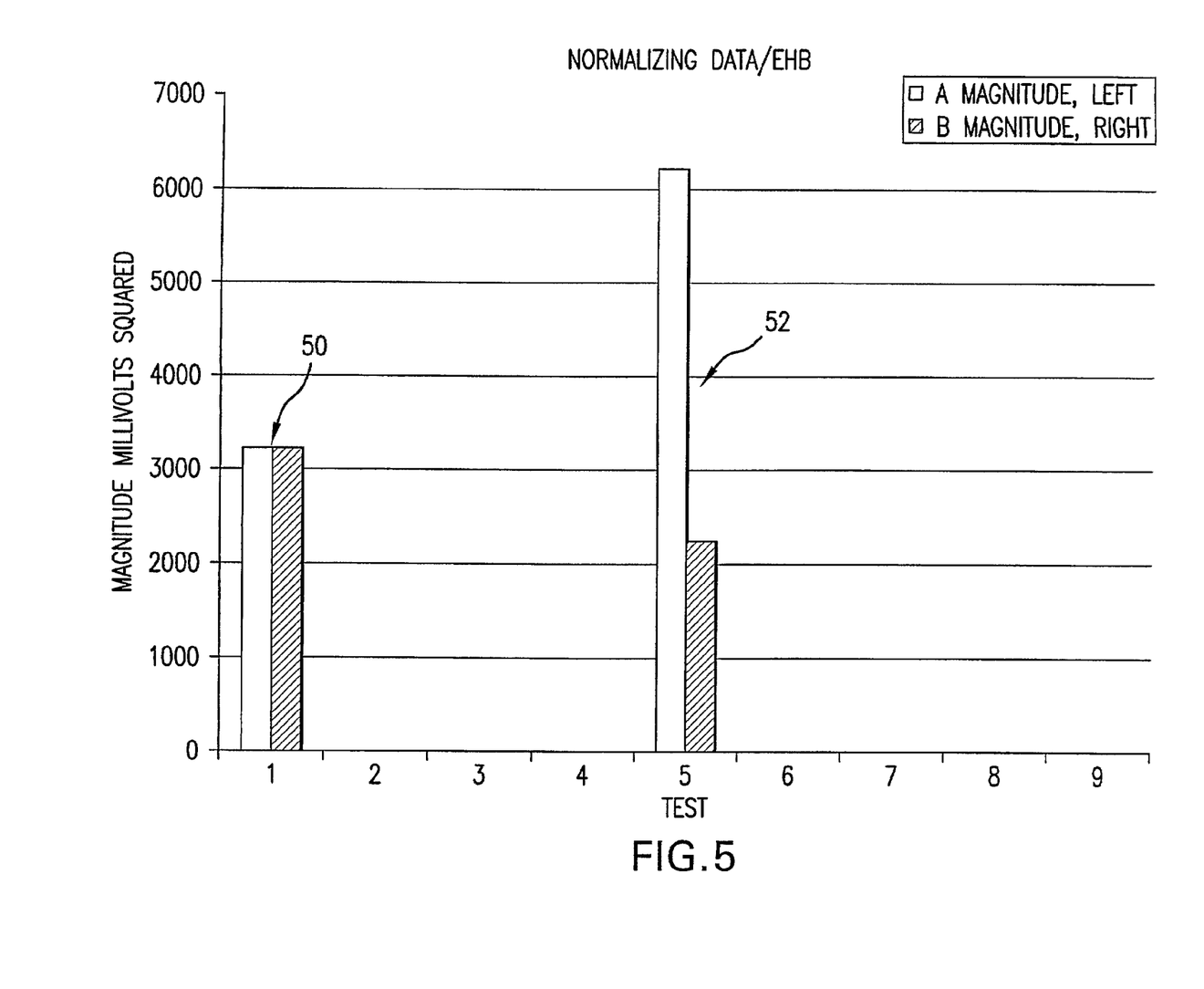
FIG. 5 is a bar graph showing the frequency domain outputs at the fundamental pulse frequency for the baseline and stimulated conditions.

The bar graph in FIG. 5 shows the same data as shown in FIGS. 4A-D. The left hand graph 50 is for the baseline condition (FIGS. 4A-B), and the right hand graph 52 is for the stimulated condition (FIGS. 4C-D). This representation of the data shows the significant increase in pulse magnitude in the left sensor as compared to the right sensor using the frequency domain method.

Figure 6:
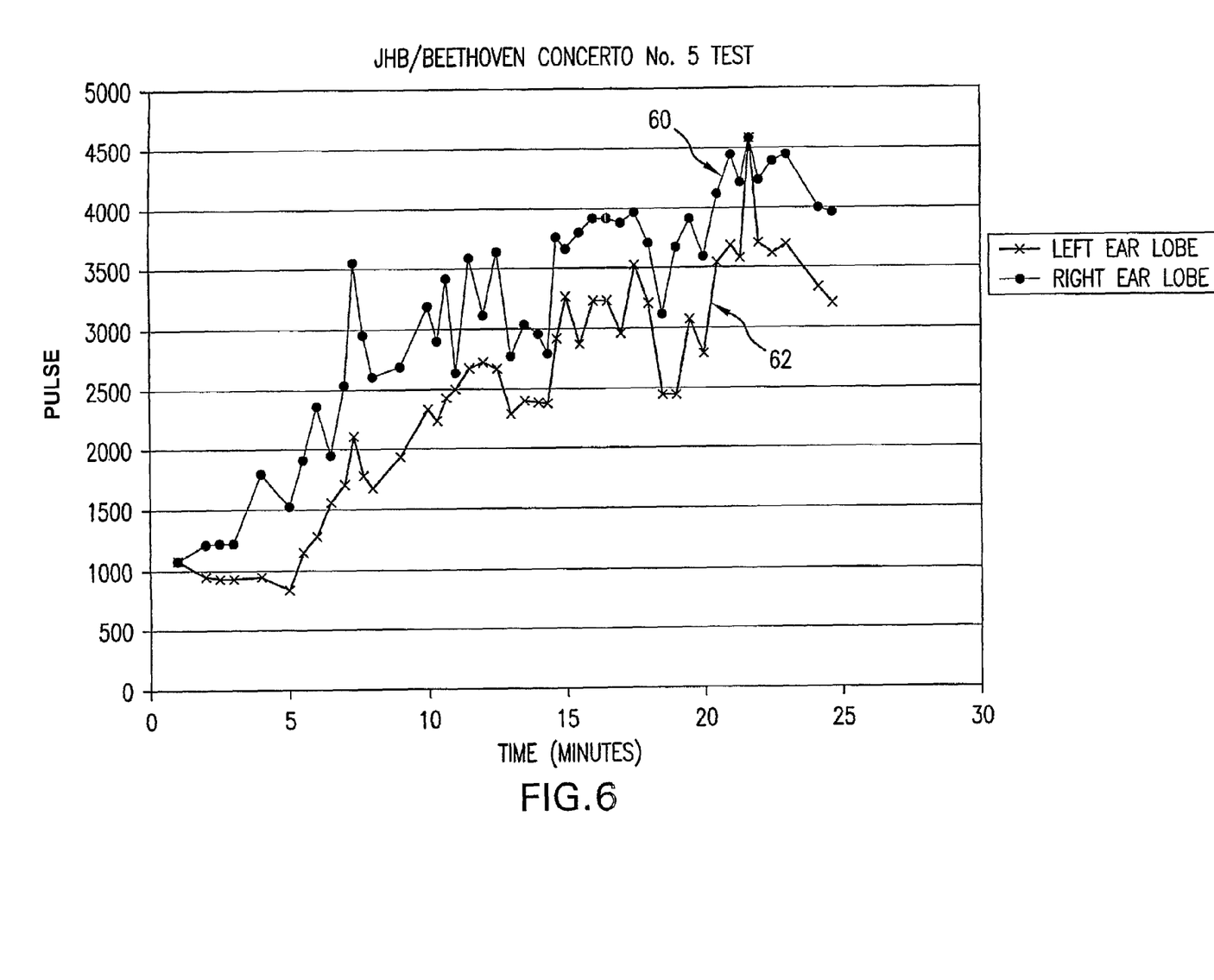
FIG. 6 is a time series plot of outputs from the left and right sides when a subject listens to the Beethoven Concerto No. 5.

FIG. 6 shows a time series plot of the right earlobe pulse 60 and the left earlobe 62 generated when a subject listened to the Beethoven Concerto No. 5 while lying supine with eyes closed. The figure shows the significant increase of pulse magnitude for the left earlobe as compared to the right earlobe, which follows findings by other investigators using PET and fMRI instrumentation.

Figure 7:
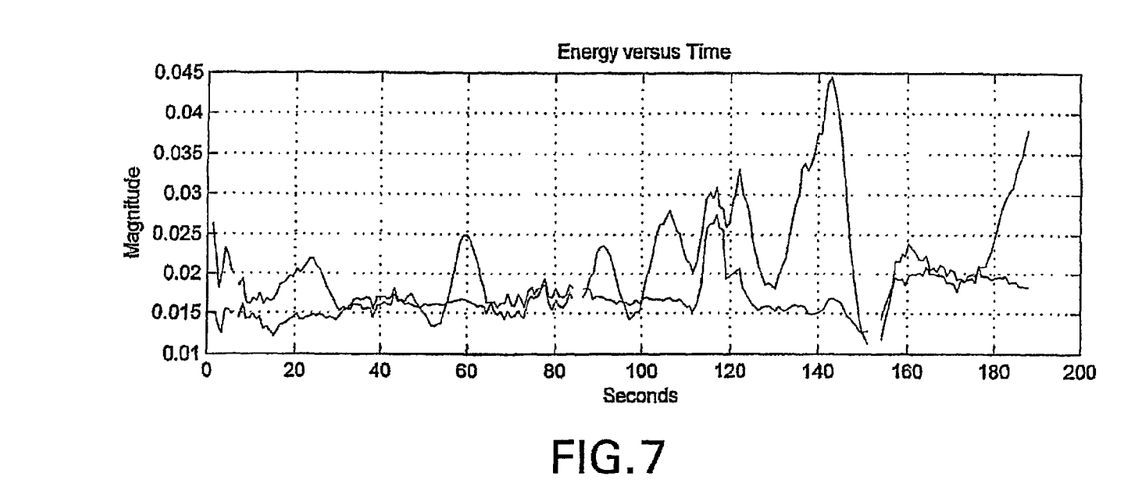
FIG. 7 is a graph showing the pulse magnitudes of left and right sides during a further test.
Figure 8:
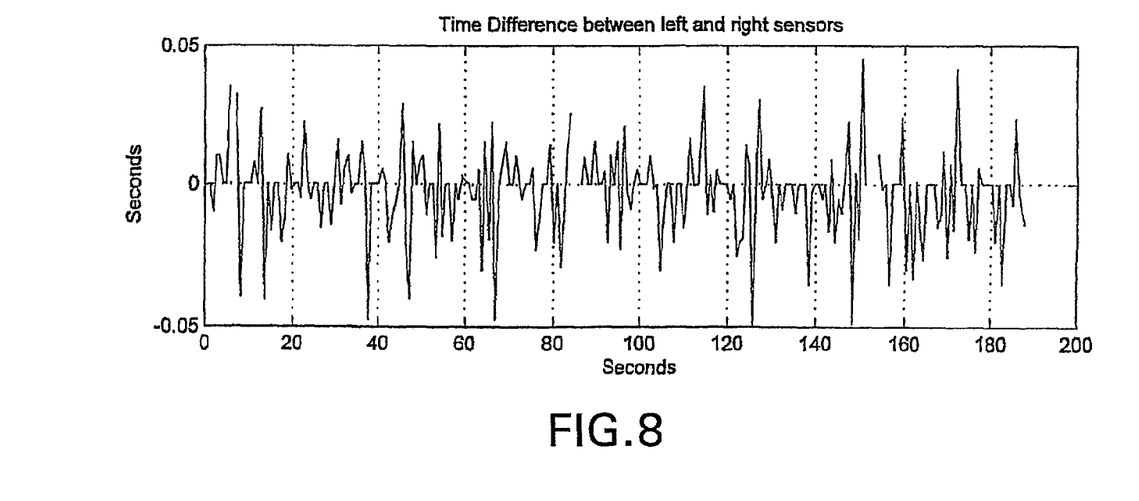
FIG. 8 is a graph showing the time difference between left and right sides during the further test of FIG. 7.

FIGS. 7 and 8 depict results of a further test. The human subject was first asked to relax (0-86 seconds), while at 76 seconds the right output was set equal to the left output. At 86 seconds the subject was asked to visualize an angel sitting on a white puffy cloud and to keep adding details to the image. The test was stopped at 152 seconds. The large increase in energy on the right side is apparent from FIG. 7. FIG. 8 shows the time difference between the left and right sides. Larger time differences are seen when the subject shifts focus during the visualization process. The data were taken at a 2 kHz sampling rate.

Figure 9:
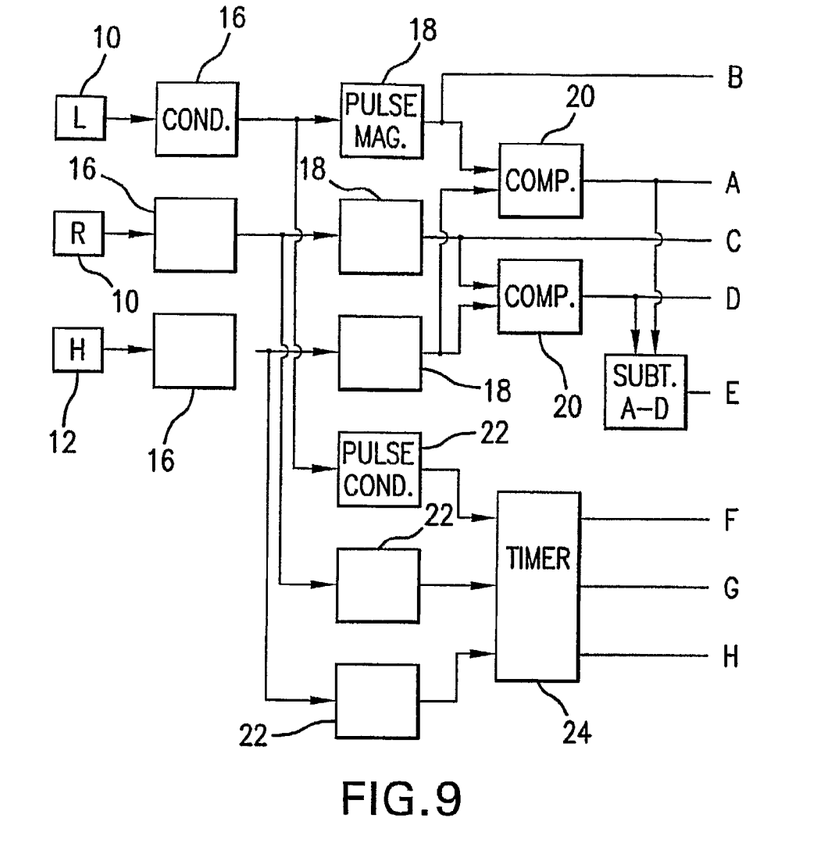
FIG. 9 is a block diagram of an analog signal processing flow for a three sensor embodiment of the present invention.

FIG. 9 is a block diagram of the analog processing electronics for the three-sensor embodiment. The arrangement is similar to that of FIG. 2 (the same element numbers are used to designate corresponding elements) with the addition of processing for the heart sensor 12. The left and right sensors 10 and heart sensor 12 feed analog conditioning circuits 16 that provide suitable power for the sensor, signal conditioning amplifier, and high and low pass filters to eliminate noise in a typical test area. The subsequent pulse magnitude detection circuit 18 measures the pulse magnitude, and feeds it to a pulse comparator circuit 20. The output of pulse comparator circuit 20 includes magnitudes of the pulses measured by the sensors 10 and the difference between these pulse magnitudes and between each and the heart. In addition, the pulse outputs from the analog circuitry 16 are conditioned in waveform by pulse conditioners 22 and fed to a timer 24. The output of timer 24 is the time difference between the arrival times of the pulses at the sensors 10. Output A is the magnitude difference between the left sensor and the heart sensor, output B is the magnitude of the left pulse, output C is the right pulse magnitude, output D is the magnitude difference between the right sensor and the heart sensor, output E is the difference between outputs A and D, output F is the time difference between the left pulse and the heart, output G is the time difference between the right pulse and the heart, and output H is time difference between outputs F and G.

Figure 10:
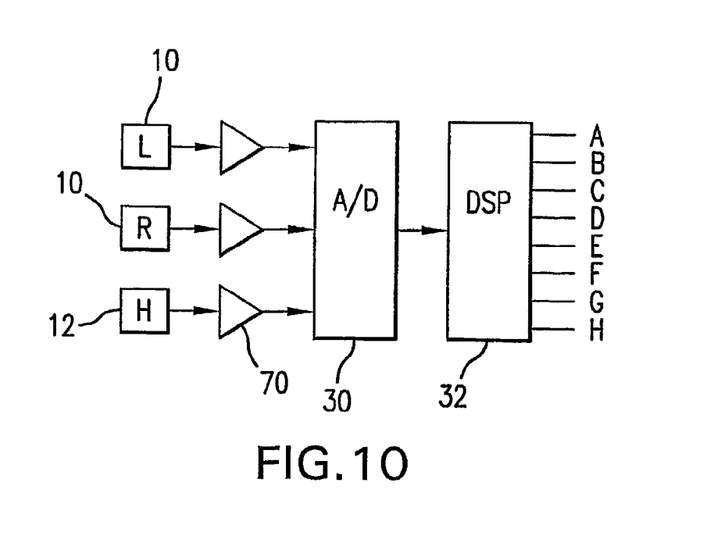
FIG. 10 is a block diagram of a digital signal processing flow for a three sensor embodiment of the present invention.

FIG. 10 is a block diagram of a digital signal processing flow for a three sensor embodiment. In this arrangement, a third sensor 12 is placed over the heart. The heart-to earlobe-pulses are processed with the same software. This measurement provides an absolute measurement of brain activity since all measurements are related to the heart output measurement which is the driver for the entire arterial system. The processing electronics is similar to that of FIG. 3 (the same element numbers are used to designate corresponding elements) with the addition of processing for the heart sensor 12. Amplifiers 70 may be added between the sensors and A/D converter 30. The processing is similar to that of FIG. 3 and the outputs are the same as explained above in relation to the analog embodiment.

While embodiments of the present invention have been described in the foregoing specification and drawings, it is to be understood that the present invention is defined by the following claims when read in light of the specification and drawings.

I claim:

1. A method of measuring human brain activity, comprising the steps of:
   simultaneously measuring pulses at two locations on a human subject that each receives blood from a different carotid artery or branch thereof that feeds a respective one of left and right hemispheres of the brain of the human subject;
   determining pulse characteristics from the measured pulses, the pulse characteristics including (1) amplitudes of the measured pulses, (2) differences between the amplitudes of the measured pulses, and (3) time differences between the measured pulses; and
   evaluating relative left and right hemisphere activity of the brain of the human subject based on the determined pulse characteristics.

2. The method of claim 1, wherein the step of measuring pulses includes placing pulse sensors on left and right earlobes of the human subject.

3. The method of claim 2, wherein the pulse sensors transmit infrared energy through the respective earlobe.

4. The method of claim 1, wherein the step of measuring pulses includes placing pulse sensors on left and right sides of a forehead of the human subject.

5. The method of claim 1, wherein the step of measuring pulses includes placing pulse sensors on left and right sides of a neck of the human subject adjacent to the respective carotid artery or branch thereof.

6. The method of claim 1, wherein the step of measuring pulses includes using pulse sensors that are selected from the group consisting of optical sensors, RF displacement sensors, capacitance displacement sensors, pressure sensors, acoustic distance sensors, acoustic Doppler flow sensors, and optical displacement sensors.

7. The method of claim 1, further comprising the step of disproportionately stimulating brain activity in the left and right hemispheres of the brain of the human subject during the step of measuring pulses.

8. The method of claim 1, further comprising the step of wirelessly transmitting the measured pulses to a receiver remote from the human subject during the step of measuring pulses, and performing the determining and evaluating steps with a processor attached to the receiver.

9. The method of claim 1, further comprising the step of setting results of measurements at the two locations equal to each other during a period of mental relaxation of the human subject before the step of measuring pulses.

10. The method of claim 1, wherein the determining step further comprises the step of removing low frequency noise outside a 0.75-2.0 Hz operating band caused by motion or physiological changes of the human subject.

11. The method of claim 1, wherein the step of measuring pulses includes placing the human subject in one of a standing and sitting position.

12. The method of claim 1, wherein the differences between the amplitudes of the measured pulses are measured at a peak pulse frequency.

13. A method of measuring human brain activity, comprising the steps of:
   simultaneously measuring pulses at three locations on a human subject, the first and second locations each receiving blood from a different carotid artery or a branch thereof that feeds a respective one of left and right hemispheres of the brain of the human subject, and the third location being adjacent to the heart of the human subject;
   determining pulse characteristics from the measured pulses, the pulse characteristics including (1) amplitudes of the measured pulses, (2) differences among the amplitudes of the measured pulses, and (3) time differences among the measured pulses; and
   evaluating relative and absolute left and right hemisphere activity of the brain of the human subject based on the determined pulse characteristics.

14. The method of claim 13, wherein the step of measuring pulses includes placing pulse sensors on left and right earlobes of the human subject.

15. The method of claim 13, wherein the step of measuring pulses includes placing pulse sensors on left and right sides of a forehead of the human subject.

16. The method of claim 13, wherein the step of measuring pulses includes placing pulse sensors on left and right sides of a neck of the human subject adjacent to the respective carotid artery or branch thereof.

17. The method of claim 13, further comprising the step of disproportionately stimulating brain activity in the left and right hemispheres of the brain of the human subject during the step of measuring pulses.

18. The method of claim 13, further comprising the step of wirelessly transmitting the measured pulses to a receiver remote from the human subject during the step of measuring pulses, and performing the determining and evaluating steps with a processor attached to the receiver.

19. The method of claim 13, further comprising the step of setting results of measurements at the first and second locations equal to each other during a period of mental relaxation of the human subject before the step of measuring pulses.

20. The method of claim 13, wherein the determining step further comprises the step of removing low frequency noise outside a 0.75-2.0 Hz operating band caused by motion or physiological changes of the human subject.

* * * * *